United States Patent [19]

Takizawa et al.

[11] Patent Number: 4,894,137

[45] Date of Patent: Jan. 16, 1990

[54] ENZYME ELECTRODE

[75] Inventors: Koichi Takizawa; Satoshi Nakajima, both of Kyoto; Masato Arai, Muko, all of Japan

[73] Assignee: Omron Tateisi Electronics Co., Kyoto, Japan

[21] Appl. No.: 95,977

[22] Filed: Sep. 14, 1987

[30] Foreign Application Priority Data

| Sep. 12, 1986 | [JP] | Japan | 61-216391 |
| Sep. 17, 1986 | [JP] | Japan | 61-220018 |
| Oct. 3, 1986 | [JP] | Japan | 61-236870 |
| Oct. 6, 1986 | [JP] | Japan | 61-237298 |
| Oct. 27, 1986 | [JP] | Japan | 61-255294 |
| Oct. 29, 1986 | [JP] | Japan | 61-257868 |
| Nov. 25, 1986 | [JP] | Japan | 61-280346 |

[51] Int. Cl.$^4$ ............................................. C12Q 1/00
[52] U.S. Cl. ................................. 204/403; 435/288; 435/817
[58] Field of Search ............... 204/403, 1 E; 435/291, 435/817, 288; 128/635

[56] References Cited

U.S. PATENT DOCUMENTS

| 3,838,034 | 9/1974 | Groves | 435/291 X |
| 4,020,830 | 5/1977 | Johnson et al. | 204/403 X |
| 4,073,713 | 2/1978 | Newman | 204/1 T X |
| 4,218,298 | 8/1980 | Shimada et al. | 204/403 X |
| 4,225,410 | 9/1980 | Pace | 435/817 X |
| 4,356,074 | 10/1982 | Johnson | 204/1 T X |
| 4,404,066 | 9/1983 | Johnson | 204/1 T |
| 4,508,613 | 4/1985 | Busta et al. | 204/418 |
| 4,534,356 | 8/1985 | Papadakis | 128/635 |
| 4,552,840 | 11/1985 | Riffer | 435/14 |
| 4,655,880 | 4/1987 | Liu | 204/1 T |
| 4,713,165 | 12/1987 | Conover et al. | 204/403 |

FOREIGN PATENT DOCUMENTS

| 141550 | 11/1981 | Japan | 204/403 |
| 29658 | 2/1985 | Japan | 204/403 |
| 1442303 | 7/1976 | United Kingdom . | |

Primary Examiner—G. L. Kaplan
Attorney, Agent, or Firm—Wegner & Bretschneider

[57] ABSTRACT

An enzyme electrode comprising: an insulative base plate; two or more electrodes formed on the surface of the insulative base plate and each having an exposed portion; an insulative protection film to insulate and protect the electrodes excluding at least those exposed portions; and an immobilized enzyme film to integratedly cover the exposed portions.

20 Claims, 18 Drawing Sheets

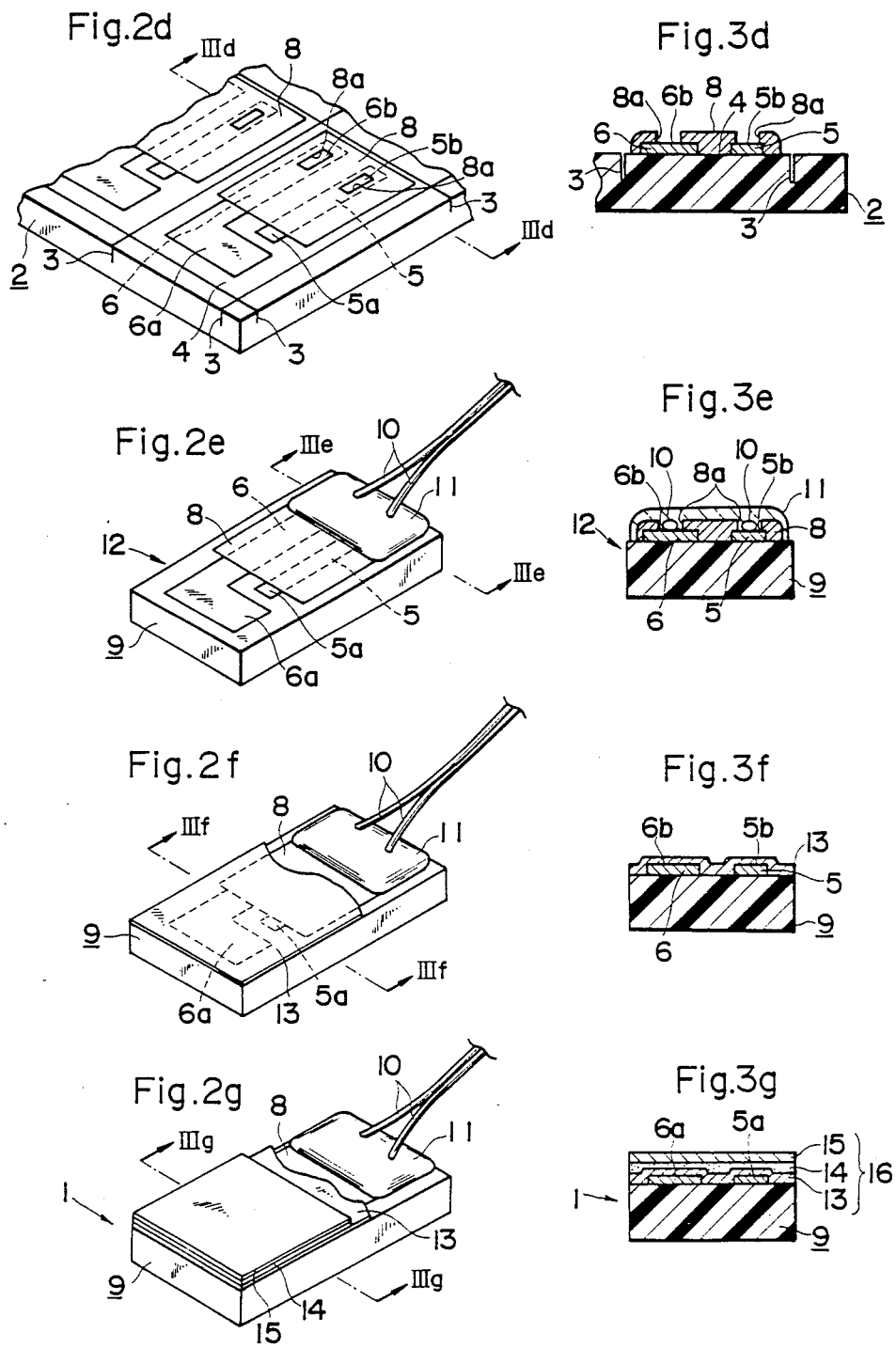

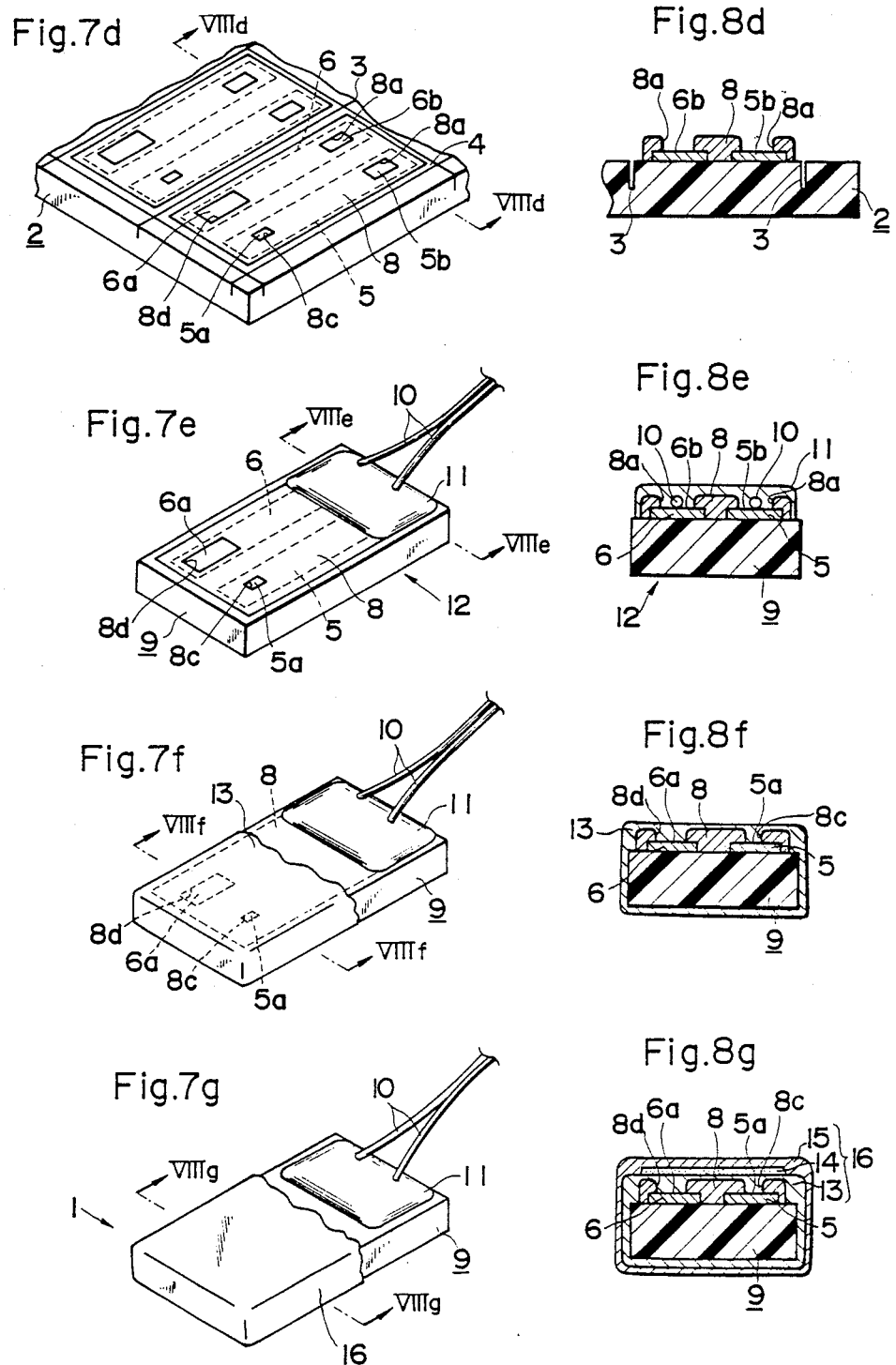

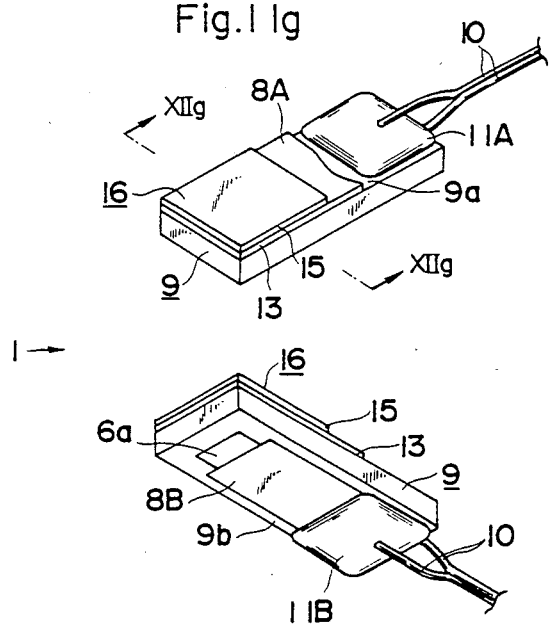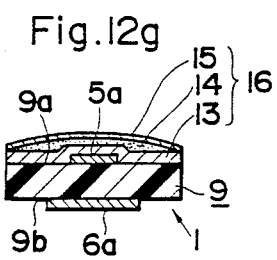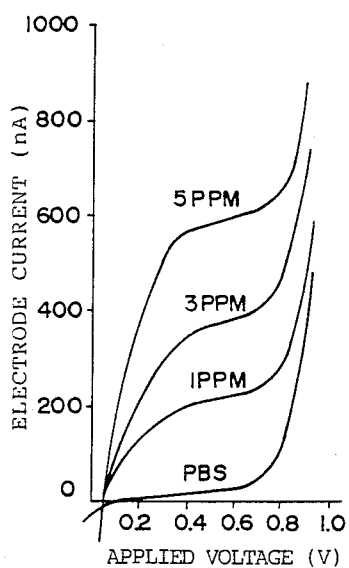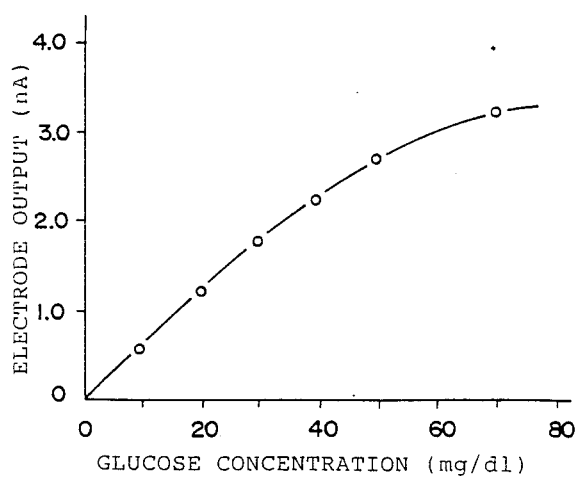

ENZYME ELECTRODE

BACKGROUND OF THE INVENTION

1. Field of the Invention

The present invention relates to an enzyme electrode to electrically measure through an enzyme reaction a concentration of a specified chemical material contained in a liquid to be examined and serving as a substrate of the enzyme. The invention also relates to a method of manufacturing such an enzyme electrode.

2. Prior Art Statement

As a conventional enzyme electrode, such an enzyme electrode as shown in FIG. 1e has been known. A structure of this conventional enzyme electrode will be described together with its manufacturing method with reference to FIGS. 1a to 1e.

FIG. 1a shows a state in which lead wires 110 are connected to a working electrode 105 and a reference electrode 106 by soldering, respectively. The working electrode 105 is made of platinum and is formed like a pin having a circular cross section. The reference electrode 106 is made of silver and is formed like a cylinder having a hollow portion 106b.

FIG. 1b shows a state in which the working electrode 105 and reference electrode 106 are enclosed in a cup-shaped casing 109. The reference electrode 106 is inserted into the casing 109 from an opening 109a of the casing 109. The working electrode 105 is supported by a supporting member 107 in the hollow 106b of the reference electrode 106 so as to be insulated from the reference electrode 106. The reference electrode 106 and working electrode 105 are coaxially arranged. Lead wires 110 are pulled out to the outside from a hole 109b formed on the bottom portion of the casing 109.

FIG. 1c shows a state in which an epoxy resin 108 is filled in the casing 109. The epoxy resin 108 overflows on the opening portion 109a of the casing 109, thereby completely covering the working electrode 105 and reference electrode 106. It takes about six days at room temperature until the epoxy resin is hard.

FIG. 1d shows a state in which the upper surface of the assembly shown in FIG. 1c is ground and polished together with the casing 109 and worked so as to form a spherical surface, the edge surfaces of the working electrode 105 and reference electrode 106 are exposed, and these edge surfaces are used as exposed portions 105a and 106a, respectively. A diameter of working electrode 105 and inner and outer diameters of reference electrode 106 are determined such that the ratio of the areas of the exposed portions 105a and 106a become a predetermined value.

FIG. 1e shows an enzyme electrode which is completed by attaching an immobilized enzyme film 111 to the assembly shown in FIG. 1d. The film 111 is made by immobilizing an enzyme (e.g., glucose oxidase or the like) to detect a specified chemical material serving as a substrate to a high molecular film. The film 111 is coated onto the polished surface so as to be closely adhered to the exposed portions 105a and 106a. The peripheral edge portion of the film 111 is fixed to the outer surface of the casing 109 by an O ring 112. A groove 109c to fix the O ring 112 is formed in the outer peripheral surface of the casing 109.

The foregoing conventional enzyme electrode is produced one by one by the hand work and its mass production is difficult. In addition, this hand work consists of continuous fine works and has drawbacks such that the material is damaged or left in vain, in particular, the electrode material is frequently damaged and a large amount of electrode material is left in vain and the yield is low. Further, there are inconveniences such that the working cost and manufacturing costs are high. The working cost occupies 60 to 80% of the manufacturing cost.

In addition, since the immobilized enzyme film 111 used is provided to integrally cover the exposed portions 105a and 106a of both electrodes, the film 111 having a large area is necessary. There is an inconvenience such that the final cost of the enzyme electrode rises because the immobilized enzyme film itself is expensive.

On the other hand, the foregoing conventional enzyme electrode has the following problems when it is used.

When the exposed portions 105a and 106a are formed by grinding and polishing, cracks and gaps are formed in the epoxy resin 108 around the working electrode 105. This is because of the differences of hardness among the epoxy resin 108, working electrode 105, and reference electrode 106. If the water or other liquid enters the cracks or graps when the enzyme electrode is used, the noise is generated and the measuring accuracy deteriorates.

An output of the enzyme electrode is determined by the areas of the exposed portions 105a and 106a (especially, the area of the exposed portion 105a of the working electrode 105). The exposed portions 105a and 106a are made by the hand work, so that a variation of areas of the exposed portions 105a and 106a occurs and the outputs also vary.

Further, an output variation is caused due to the defective attachment of the immobilized enzyme film 111.

Since one kind of immobilized enzyme film 111 is attached, the foregoing conventional enzyme electrode has an inconvenience such that it cannot be used to measure many items.

There are also inconveniences such that the foregoing conventional enzyme electrode is cylindrical and a degree of freedom of the shape is small, there is a limitation when designing an apparatus for clinical examinations or the like using this enzyme electrode, namely, the easiness of use of such an enzyme electrode is poor, and the like.

SUMMARY OF THE INVENTION

It is an object of the present invention to provide an enzyme electrode in which the mass production can be performed, the cost is low, and the performance is excellent and to provide a method of manufacturing such an enzyme electrode.

Another object of the present invention is to provide an enzyme electrode which can measure many items.

Still another object of the present invention is to provide an enzyme electrode which is excellent in easiness of use.

An enzyme electrode according to the present invention comprises: an insulative base plate; two or more electrodes provided on the surface of the insulative base plate and each having an exposed portion; an insulative protection film to insulatively protect the electrodes excluding at least the exposed portions; and an immobilized enzyme film to integratedly cover the exposed portions.

A method of manufacturing an enzyme electrode according to the present invention comprises the steps of: dividing the surface of an insulative flat plate into a plurality of segments; forming in each segment two or more electrodes each having the portion serving as an exposed portion; forming a photosensitive resin film to cover the electrodes onto the surface of the insulative flate plate; eliminating the portions which cover the exposed portions by exposing the photosensitive resin film by use of a photo mask, thereby forming an insulative protection film which covers the other portions of the electrodes; separating the insulative flat plate into a plurality of segments, thereby forming individual insulative base plates; and forming an immobilized enzyme film to integratedly cover the exposed portions onto the surfaces of the insulative base plates.

According to the present invention, a plurality of enzyme electrodes can be simultaneously manufactured on a single insulative flat plate and the mass production can be realized. On the other hand, there are advantages such that the steps of manufacturing enzyme electrodes can be easily automated and the manufacturing cost can be reduced. Further, there is also an advantage such that the yield can be improved since the loss of material is little in the manufacturing steps.

On the other hand, with respect to the performance of the enzyme electrode, since the grinding and polishing steps of the electrodes are not included in the manufacturing steps, cracks and gaps into which a liquid can enter are not formed in the peripheral portion of the electrode and the noise decreases. Since the area of each exposed portion (particularly, the area of the exposed portion of the working electrode) is determined with high accuracy by the photo mask and a number of enzyme electrodes are together manufactured by the mass production, the areas of the exposed portions of the electrodes are uniform and a variation in output decreases. Further, since the immobilized enzyme film is integratedly formed on the surface of the insulative base plate, a change in output due to the defective attachment of the immobilized enzyme film is small and the output is stabilized.

The above and other objects, features and advantages of the present invention will become apparent from the following detailed description of the embodiments with reference to the accompanying drawings.

BRIEF DESCRIPTION OF THE DRAWINGS

FIGS. 2a to 2g and 3a to 3g show manufacturing steps of an enzyme electrode of the first embodiment of the present invention;

FIGS. 2a to 2g are perspective views showing the manufacturing steps in accordance with the order of the steps;

FIGS. 3a to 3d are enlarged cross sectional views taken along the line IIIa—IIIa in FIG. 2a, the line IIIb—IIIb in FIG. 2b, the line IIIc—IIIc in FIG. 2c and the line IIId—IIId in FIG. 2d, respectively, and each diagram illustrates a part of the cross sectional portion;

FIGS. 3e, 3f and 3g are enlarged cross sectional views taken along the line IIIe—IIIe in FIG. 2e, the line IIIf—IIIf in FIG. 2f and the line IIIg—IIIg in FIG. 2g, respectively;

FIGS. 7a to 7g and 8a to 8g show manufacturing steps of an enzyme electrode of the second embodiment of the present invention;

FIGS. 7a to 7g are perspective views showing the manufacturing steps in accordance with the order of the steps;

FIGS. 8a to 8d show enlarged cross sectional views taken along the line VIIIa—VIIIa in FIG. 7a, the line VIIIb—VIIIb in FIG. 7b, the line VIIIc—VIIIc in FIG. 7c and the line VIIId—VIIId in FIG. 7d, respectively, and each diagram shows a part of the cross sectional portion;

FIGS. 8e to 8g are enlarged cross sectional views taken along the line VIIIe—VIIIe in FIG. 7e, the line VIIIf—VIIIf in FIG. 7f, and the line VIIIg—VIIIg in FIG. 7g, respectively.

FIGS. 11a to 11g and 12a to 12g show manufacturing steps of an enzyme electrode of the third embodiment of the invention;

FIGS. 11a to 11g are perspective views showing the manufacturing steps in accordance with the order of the steps;

FIGS. 12a to 12e are enlarged cross sectional views taken along the line XIIa—XIIa in FIG. 11a, the line XIIb—XIIb in FIG. 11b, the line XIIc—XIIc in FIG. 11c, the line XIId—XIId in FIG. 11d and the line XIIe—XIIe in FIG. 11e, respectively, and each diagram illustrates a part of the cross sectional portion;

FIGS. 12f and 12g are enlarged cross sectional views taken along the line XIIf—XIIf in FIG. 11f and the line XIIg—XIIg in FIG. 11g, respectively;

FIG. 13 is a graph showing the characteristic of an unfinished electrode of the enzyme electrode of the third embodiment;

FIG. 14 is a graph showing the measured characteristic of the enzyme electrode of the third embodiment;

FIG. 15a is a perspective view of the whole enzyme electrode;

FIGS. 15b and 15c are enlarged cross sectional views taken along the lines XVb—XVb and XVc—XVc in FIG. 15a, respectively;

FIGS. 16a to 16e are perspective views showing the manufacturing steps in accordance with the order of the steps;

FIGS. 17a to 17d are enlarged cross sectional views taken along the line XVIIa—XVIIa in FIG. 16a, the line XVIIb—XVIIb in FIG. 16b, the line XVIIc—XVIIc in FIG. 16c and the line XVIId—XVIId in FIG.

Figure 16A:
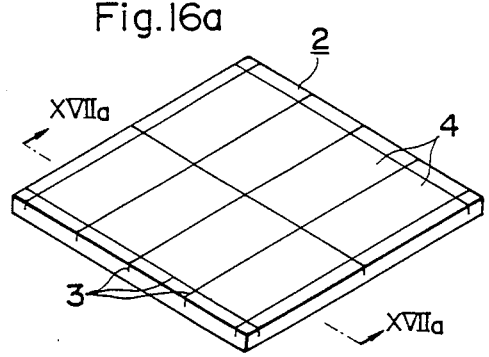
FIGS. 16a to 16e and 17a to 17e show the manufacturing steps of working portions of the enzyme electrode of the fourth embodiment of the present invention.
Figure 16B:
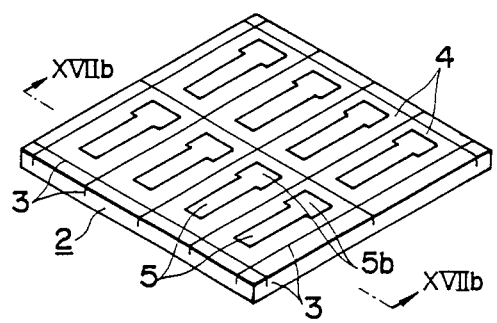
Figure 16C:
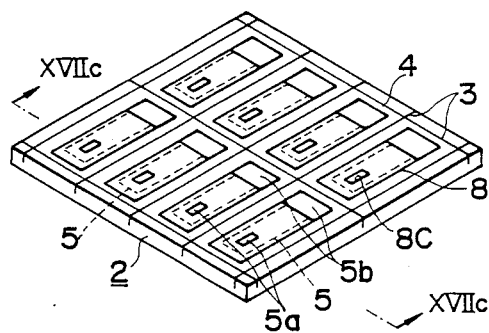
Figure 17C:
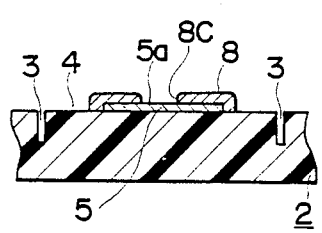
Figure 16D:
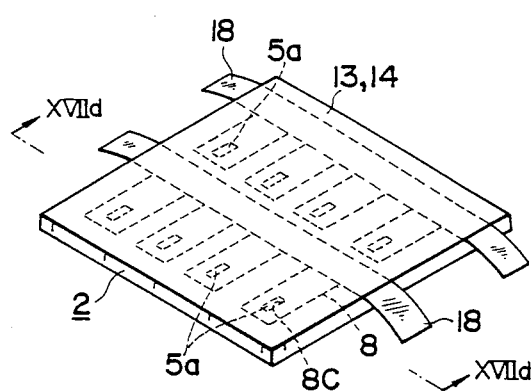
Figure 17D:
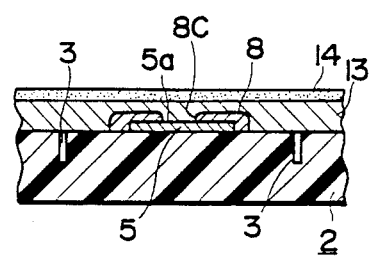
Figure 16E:
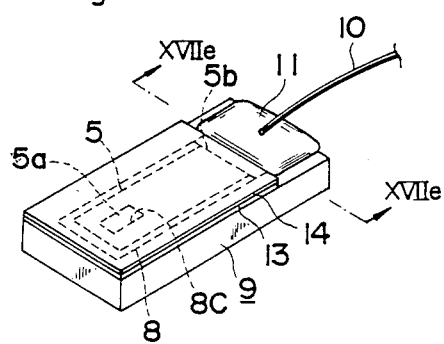
Figure 17E:
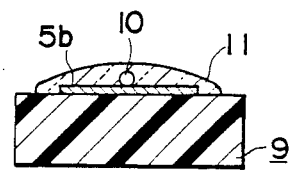
Figure 18:
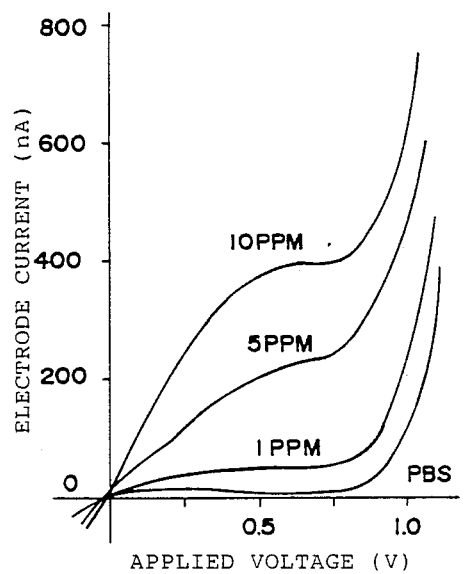
Figure 19:
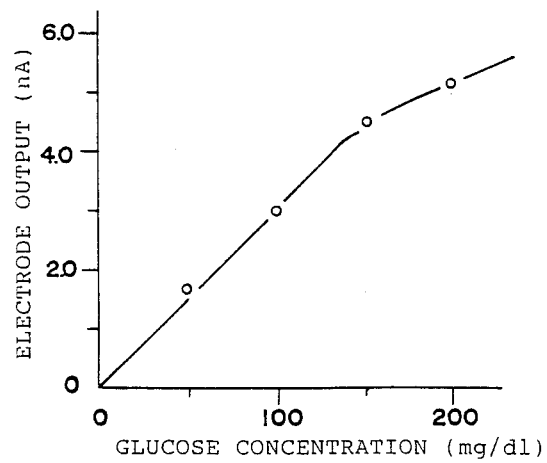
Figure 20:
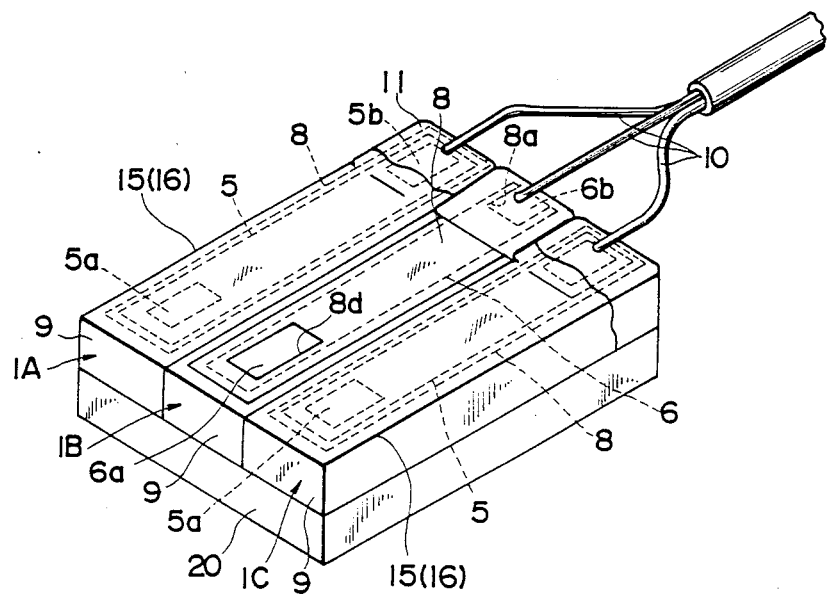
Figure 21:
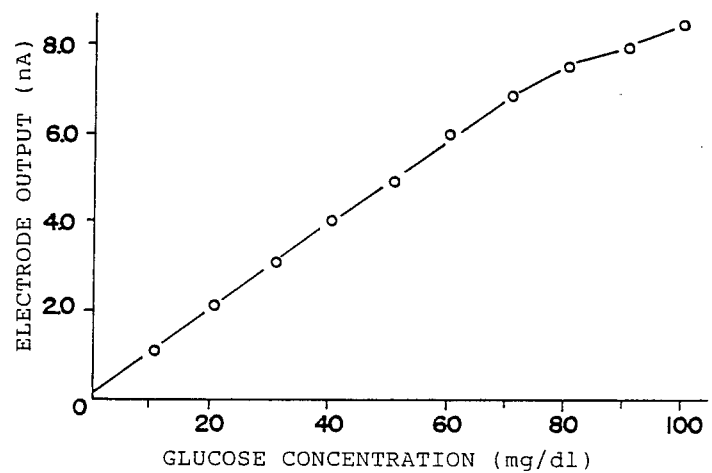
Figure 22:
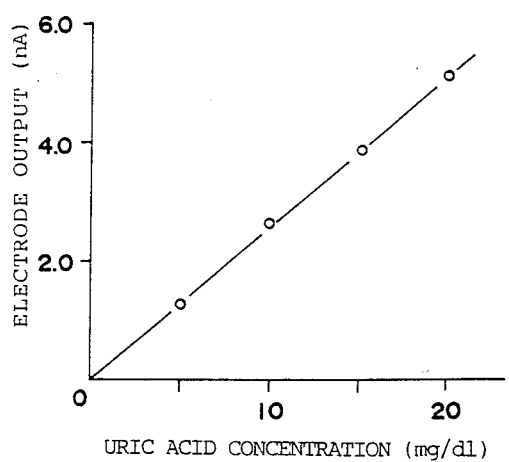
Figure 23A:
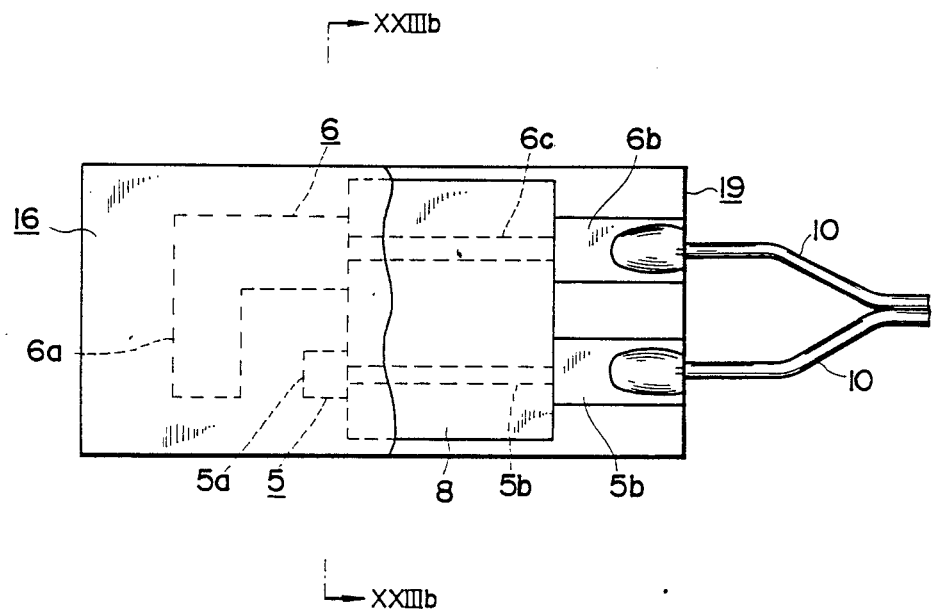
Figure 23B:
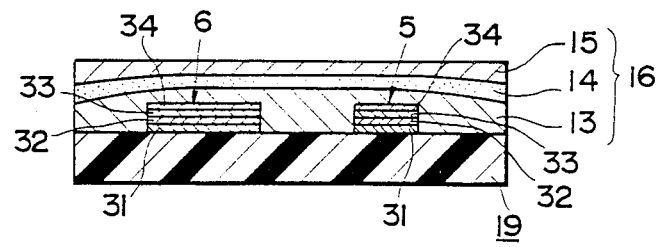
Figure 24A:
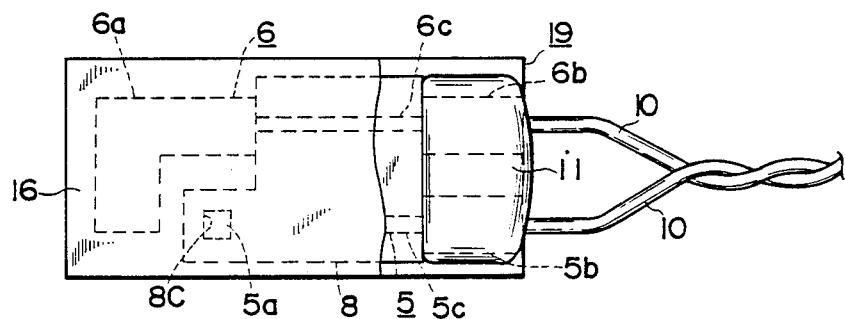
Figure 24B:
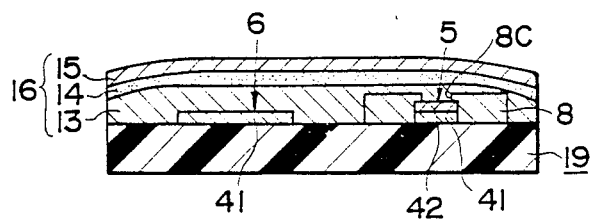

16d, respectively, and each diagram illustrates a part of the cross sectional portion;

FIG. 17e is an enlarged cross sectional view taken along the line XVIIe—XVIIe in FIG. 16e;

FIG. 18 is a graph showing the characteristic of an unfinished electrode of the enzyme electrode of the fourth embodiment;

FIG. 19 is a graph showing the measured characteristic of the enzyme electrode of the fourth embodiment;

FIG. 20 is a perspective view with a part cut away showing an enzyme electrode of the fifth embodiment of the present invention;

FIG. 21 is a graph showing the glucose concentration detection characteristic measured by use of the enzyme electrode of the fifth embodiment;

FIG. 22 is a graph showing the uric acid concentration detection characteristic measured by use of the enzyme electrode of the fifth embodiment;

FIGS. 23a and 23b show an enzyme electrode of the sixth embodiment of the present invention;

FIG. 23a is a plan view with a part cut away;

FIG. 23b is an enlarged cross sectional view taken along the line XXIIIb—XXIIIb in FIG. 23a;

FIGS. 24a and 24b show an enzyme electrode of the seventh embodiment of the present invention;

FIG. 24a is a plan view with a part cut away; and

FIG. 24b is an enlarged cross sectional view taken along the line XXIVb—XXIVb in FIG. 24a.

DETAILED DESCRIPTION OF THE PREFERRED EMBODIMENTS

The first embodiment of the present invention will be described in detail hereinbelow with reference to FIGS. 2a to 2g and 3a to 3g.

An enzyme electrode of the first embodiment is used to detect a concentration of glucose contained in the blood or the like. The manufacturing steps of this enzyme electrode will be described in accordance with the order of the manufacturing steps, thereby clarifying its structure.

Figure 1A:
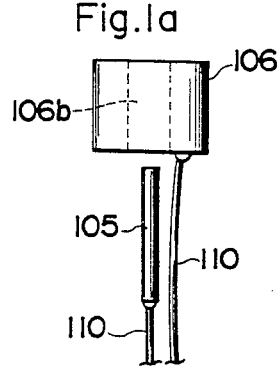
FIGS. 1a to 1e show manufacturing steps of a conventional enzyme electrode, FIG. 1a being a side elevational view and FIGS. 1b to 1e being cross sectional views.
Figure 1D:
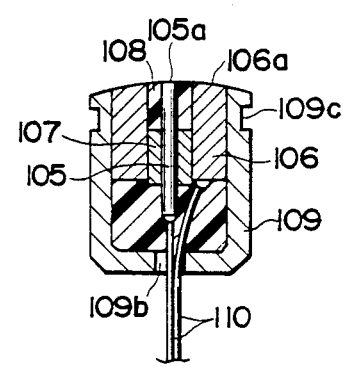
Figure 1B:
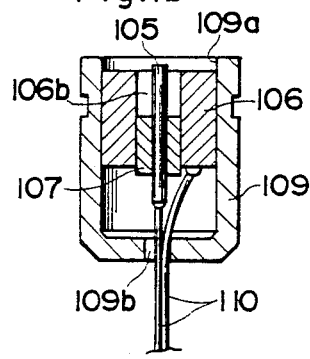
Figure 1E:
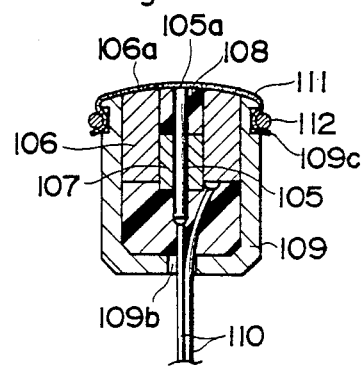
Figure 1C:
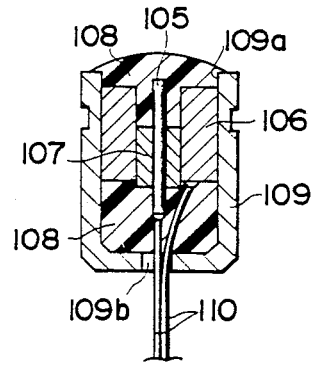
Figure 2A:
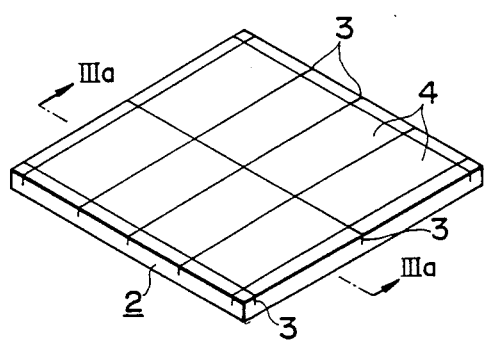
Figure 3A:
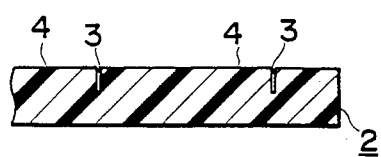

In FIGS. 2a and 3a, notches (notched segment lines) 3 are formed in the surface of an insulative flat plate 2 by a laser beam machining, so that the insulative flat plate 2 is divided into a plurality of segments 4. A depth of each notch is preferably set to about ½ of a thickness of insulative flat plate 2. An alumina ceramic plate (containing alumina of 96 weight %) having proper dimensions (e.g., 5×5cm and a thickness of 0.5mm) is used as the plate 2. Dimensions of each of the segments 4 divided by the segment lines 3 are, e.g., 4×15mm.

The material and dimensions of the plate 2 and the method of forming the segment lines 3 are not limited to those mentioned above.

Figure 2B:
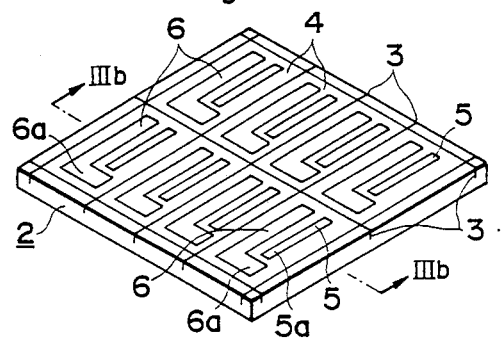
Figure 3B:
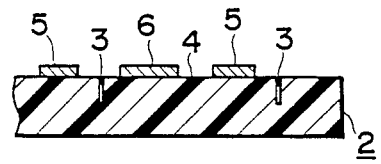

Referring now to FIGS. 2b and 3b, a working electrode 5 and a reference electrode 6 are formed on each segment 4 of the plate 2. The working electrode 5 and reference electrode 6 are the metal thin films made of platinum and have the portions serving as a working electrode exposed portion 5a and a reference electrode exposed portion 6a, respectively. The portion serving as the exposed portion 6a is slightly largely formed and extends toward the exposed portion 5a. Ranges of the exposed portions 5a and 6a are determined by the formation of an insulative protection film 8, which will be explained hereinlater. The ratio of the exposed portions 5a and 6a is, e.g., 1:20. Since the area of the working electrode exposed portion 5a exerts an influence on the characteristic of the enzyme electrode, the exposed portion 5a needs to be formed with the high accuracy. It is sufficient that the area of the reference electrode exposed portion 6a is larger than the area of the working electrode exposed portion 5a by an amount above a predetermined area. For example, the area of the exposed portion 6a is set to be twenty times as large as that of the exposed portion 5a.

The working electrode 5 and reference electrode 6 are formed by a photo resist method. The shapes of these electrodes, particularly, the shapes of their exposed portions 5a and 6a are determined by the photo mask with the high accuracy. After the photo mask was formed, platinum thin films are formed on the surface of the insulative flat plate 2 by sputtering or evaporation deposition. Both of the working electrode 5 and the reference electrode 6 are together formed on each segment 4.

Figure 2C:
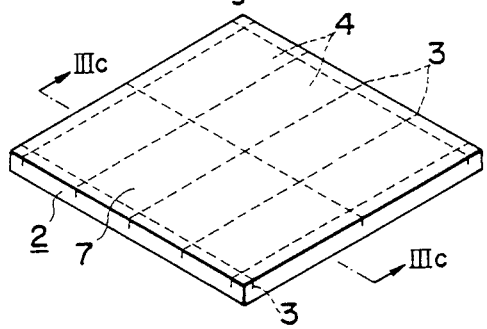
Figure 3C:
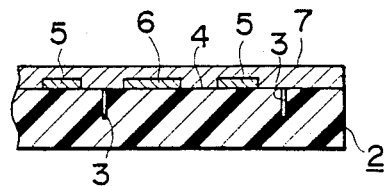

Referring now to FIGS. 2c and 3c, the whole surface of the insulative flat plate 2 on which the working electrode 5 and reference electrode 6 are formed is covered by a photosensitive polyimide film (photosensitive resin film) 7. The material of the photosensitive resin is not limited to photosensitive polyimide but may be properly changed.

Referring to FIGS. 2d and 3d, the photosensitive polyimide film 7 is exposed using the photo mask to eliminate the unnecessary portions, so that the insulative protection film 8 to protect and insulate parts of the working electrode 5 and reference electrode 6 is formed. The portions of the electrodes 5 and 6 which are not covered by the protection film 8 become the exposed portions 5a and 6a, respectively. Windows 8a are formed in the insulative protection film 8 and parts of the working electrode 5 and reference electrode 6 serving as connecting portions 5b and 6b are exposed. The insulative protection film 8 is provided for each segment 4.

Referring to FIGS. 2e and 3e, the insulative flat plate 2 is separated into a plurality of segments along the segment lines 3, so that an insulative base plate 9 is formed by each segment. The edges of lead wires 10 are soldered to the connecting portions 5b and 6b of the electrodes 5 and 6 on the insulative base plate 9. Further, an epoxy resin 11 is coated on the connecting portions 5b and 6b and the windows 8a are buried in the resin 11, thereby sealing and protecting the soldered portions of the lead wires 10. The assembly shown in FIGS. 2e and 3e is called an unfinished electrode 12.

Referring to FIGS. 2f and 3f, an acetyl cellulose film 13 is formed on the whole surface of the unfinished electrode 12 or on the surface of the unfinished electrode 12 excluding the portion of the epoxy resin 11. The exposed portions 5a and 6a of both electrodes 5 and 6 are completely covered by the film 13. The film 13 is formed in the following manner. The unfinished electrode 12 is attached to a spinner and the 3% acetyl cellulose solution (acetone:cyclohexanone=4:1) is dropped onto the surface of the insulative base plate 9. The unfinished electrode 12 is rotated for about five seconds at a rotational speed of 2,000 to 3,000 r.p.m.

Referring to FIGS. 2g and 3g, an enzyme solution is dropped onto the acetyl cellulose film 13 in the region including the portions on the exposed 5a and 6a, becoming an enzyme layer 14 by drying. The resultant assembly is further covered by an acetyl cellulose film 15, so that an enzyme electrode 1 is completed. An immobilized enzyme film 16 is constituted by the acetyl cellulose film 13, enzyme layer 14, and acetyl cellulose film 15. The acetyl cellulose film 15 is formed by the same method as that of the film 13 with use of 2% acetyl cellulose solution (acetone:ethyl alcohol=4:1).

The enzyme solution is obtained by mixing the solution in which glucose oxidase (GOD) of 2 mg is dissolved in the 0.1 M phosphoric acid buffer solution (PH 6.0) of 100 μl with the 0.5% glutaraldehyde solution of 100 μl adjusted by the same phosphoric acid buffer solution. The acetyl cellulose film 15 is provided to prevent that the high molecules such as protein and the like contained in the liquid to be examined (e.g., blood) enter the acetyl cellulose film 13 and enzyme layer 14.

The results of the tests with respect to the characteristic of the unfinished electrode 12 shown in FIGS. 2e and 3e will now be described with reference to FIG. 4. Since the performance of the enzyme electrode 1 is influenced by the characteristic of the unfinished electrode 12, it is significant to check it.

Figure 4:
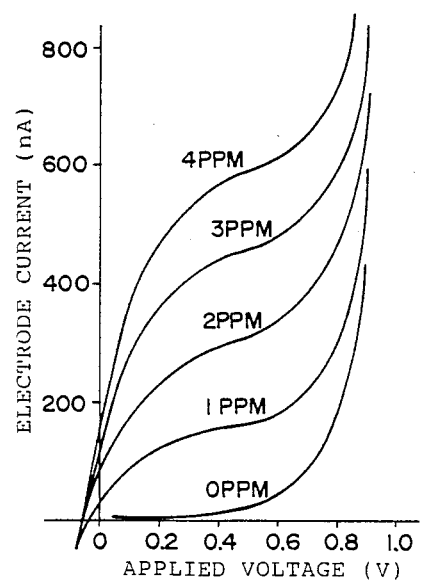
FIG. 4 is a graph showing the characteristic of an unfinished electrode of the enzyme electrode of the first embodiment.

FIG. 4 shows the relation between the applied voltage (V) and the electrode current (nA) when the unfinished electrode 12 was dipped into the phosphoric acid buffer solution containing $H_2O_2$. The parameters are the concentrations (0, 1, 2, 3 and 4 PPM) of $H_2O_2$. The size of the exposed portion 5a of the working electrode 5 is 1mm×0.5mm. Although the size of the exposed portion 5a of the working electrode 5 used exerts an influence on the characteristic, the size of the exposed portion 6a of the reference electrode 6 exerts no influence on the characteristic if it is larger than the working electrode exposed portion 5a by predetermined times. It is confirmed from this graph that the unfinished electrode 12 fairly responds to the $H_2O_2$ concentration. On the other hand, it will be understood that the proper value of the applied voltage falls within a range from 0.4 to 0.6 V.

The glucose detection characteristic of the enzyme electrode 1 in this embodiment will now be described with reference to FIGS. 5 and 6.

Figure 5:
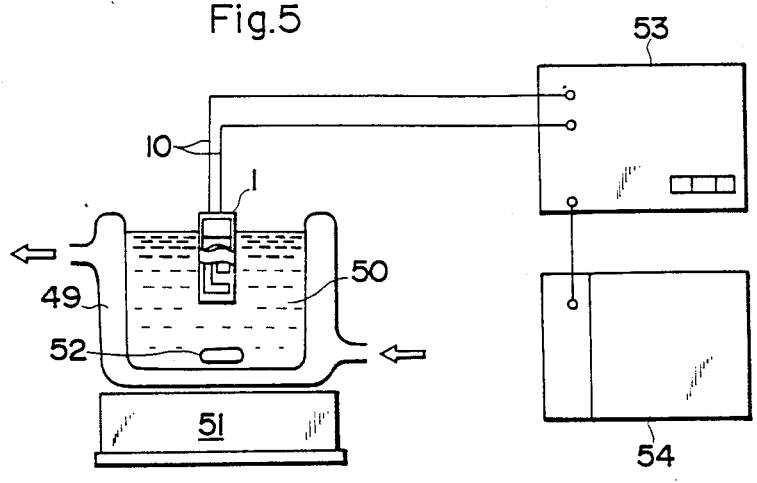
FIG. 5 shows a measuring system which is used in measurement of the characteristic of the enzyme electrode.

FIG. 5 shows a measuring system used in the measurement of the characteristic of the enzyme electrode 1. A 0.1 M phosphoric acid buffer solution 50 whose pH value is adjusted to 7.0 is stored in a constant temperature bath 49. The enzyme electrode 1 is dipped into the solution 50. The solution 50 is stirred by a stirrer 51 having a rotor 52 put in the bath 49.

The lead wires 10 of the enzyme electrode 1 are connected to an electron meter 53. A predetermined voltage (0.5 V in this measurement) is applied between the lead wires 10. A recorder 54 is connected to the electron meter 53 and an output (current) of the enzyme electrode 1 is recorded.

A predetermined amount of glucose solution is dropped into the phosphoric acid buffer solution 50 by a micropipet. Glucose (Glc) causes the following reaction in the immobilized enzyme film 16 of the enzyme electrode 1.

$H_2O_2$ causes the working electrode exposed portion 5a and reference electrode exposed portion 6a to be reacted, so that a current corresponding to the $H_2O_2$ concentration flows across both electrodes 5 and 6.

Figure 6:
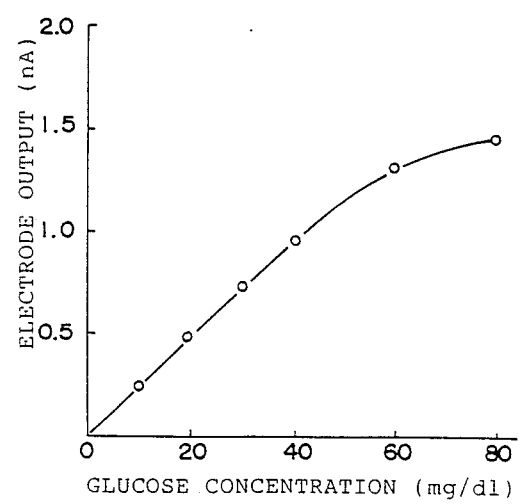
FIG. 6 is a graph showing the measured characteristic of the enzyme electrode of the first embodiment.
Figure 8A:
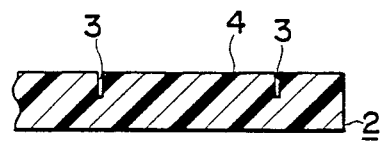

FIG. 6 shows a graph in which an output current (nA) is plotted by small circles for several glucose concentrations (mg/dl). On the other hand, a curve shown in FIG. 6 denotes an analytical curve which is obtained by connecting the plotted points. An arbitrary object to be examined, e.g., the glucose concentration of the blood can be measured on the basis of this analytical curve.

In the embodiment, glucose oxidase has been immobilized as an enzyme to the immobilized enzyme film 16. However, the enzyme is not limited to this but may be properly changed.

In addition, the shapes, size, arrangement, etc. of the insulative base plate, working electrode, reference electrode, insulative protection film, etc. are not limited to those shown in the foregoing embodiment. Their designs can be also properly changed.

FIGS. 7a to 7g and 8a to 8g show the second embodiment of the present invention. In the diagrams, the same parts and components as those shown in the foregoing first embodiment are designated by the same reference numerals unless otherwise specified.

Figure 7A:
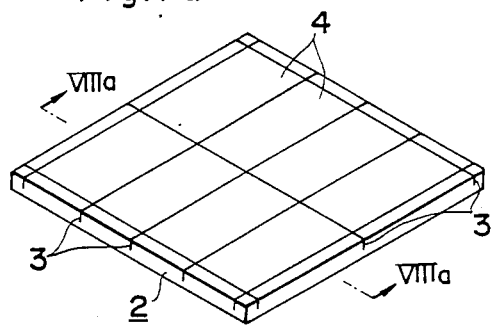
Figure 7B:
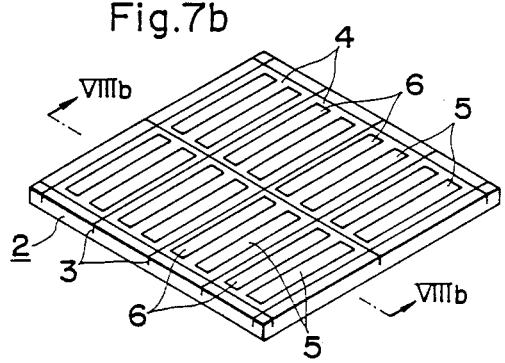
Figure 8B:
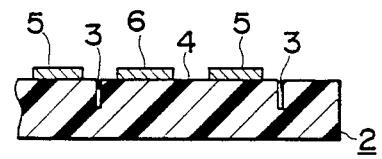
Figure 7C:
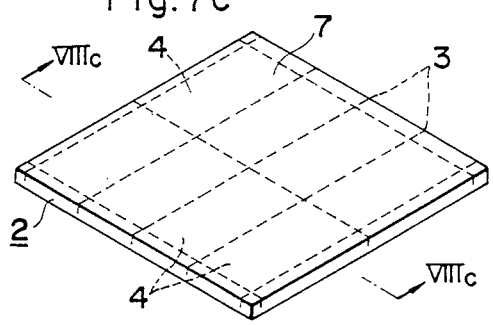
Figure 8C:
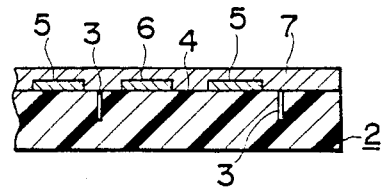

After the notches 3 were formed in the insulative flat plate 2 (refer to FIGS. 7a and 8a), the working electrode 5 and reference electrode 6 are formed in parallel on each segment 4 (see FIGS. 7b and 8b). The photosensitive resin film 7 is formed on this assembly (see FIGS. 7c and 8c). The insulative protection film 8 is formed on each segment 4 by the exposure using a photo mask. In this case, windows 8a, 8c, and 8d are simultaneously formed in the insulative protection film 8 (see FIGS. 7d and 8d). The shapes of these windows are determined with the high accuracy by the photo mask. The window 8c is formed to expose a part of the working electrode 5, thereby constituting the working electrode exposed portion 5a. The window 8d is formed to expose a part of the reference electrode 6, thereby constituting the reference electrode exposed portion 6a. The ratio of the opening areas of the windows 8c and 8d is set to 1:20 in this embodiment. The windows 8a are formed to respectively expose the other parts of the working electrode 5 and reference electrode 6, thereby constituting the connecting portions 5b and 6b to connect the lead wires 10. The shapes of these windows are not limited to those shown in the diagrams. A plurality of windows 8c and 8d may be also formed, respectively.

In a manner similar to the first embodiment, the insulative base plates 9 are formed by separating the insulative flat plate 2, the unfinished electrode 12 is formed by connecting the lead wires 10 and by protecting the connecting portions with use of the epoxy resin 11 (FIGS. 7e and 8e), thereby forming the unfinished electrode 12.

The unfinished electrode 12 is dipped into the 3% acetyl cellulose solution (acetone:cyclohexane=4:1), so that the acetyl cellulose film 13 is formed on the whole surface of the unfinished electrode 12 (FIGS. 7f and 8f). After the enzyme layer 14 covering the exposed portions 5a and 6a has been formed, the assembly is dipped into the 2% acetyl cellulose solution (acetone:ethyl alcohol=4:1) to form the acetyl cellulose film 15 on the whole surface, thereby forming the immobilized enzyme film 16 and finally forming the enzyme electrode 1 (FIGS. 7g and 8g).

Figure 9:
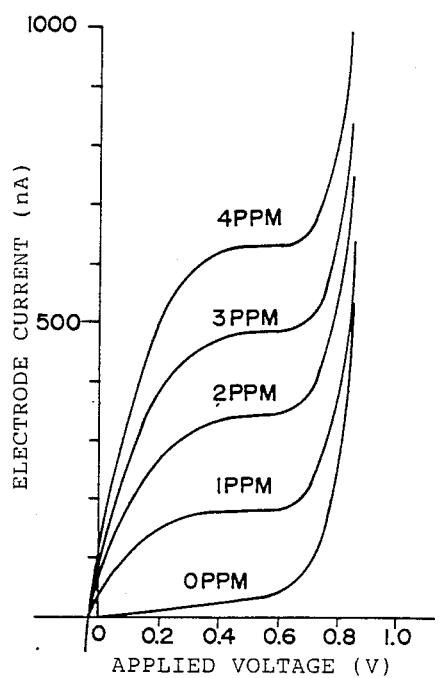
FIG. 9 is a graph showing the characteristic of an unfinished electrode of the enzyme electrode of the second embodiment.
Figure 10:
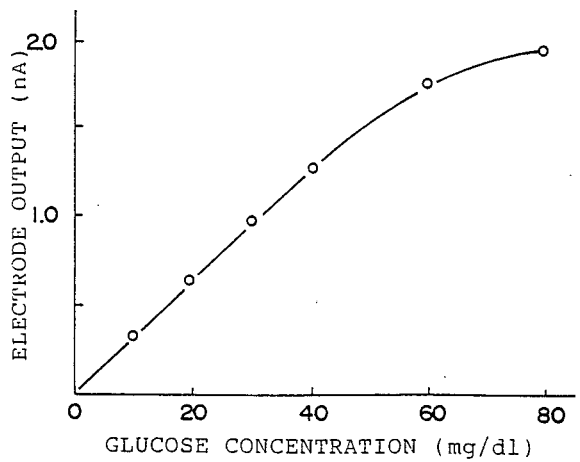
FIG. 10 is a graph showing the measured characteristic of the enzyme electrode of the second embodiment.

FIG. 9 shows the characteristic of the unfinished electrode 12 and FIG. 10 shows the characteristic of the enzyme electrode 1, respectively. These characteristics are substantially the same as those in the first embodiment shown in FIGS. 4 and 6. The size of the working electrode exposed portion 5a used is 0.4×0.6mm.

The methods of manufacturing the enzyme electrodes in the foregoing first and second embodiments can be summarized as follows.

(a) The surface of the insulative flat plate is divided into a plurality of segments.

(b) Two or more electrodes having the portions serving as the exposed portions of a predetermined area ratio are formed on the surface of each segment.

(c) A photosensitive resin film adapted to cover the electrodes is formed on the surface of the insulative flat plate.

(d) This photosensitive resin film is exposed using a photo mask and the portions which cover the exposed portions are eliminated, thereby forming an insulative protection film.

(e) The insulative flat plate is separated into a plurality of segments, thereby forming individual insulative base plates.

(f) An immobilized enzyme film is formed on the portions including the exposed portions of the surfaces of the insulative base plates, thereby integratedly covering the exposed portions.

According to this manufacturing method, a plurality of enzyme electrodes can be simultaneously manufactured on a single insulative flat plate and the mass production can be realized. In addition, there are advantages such that the manufacturing steps of the enzyme electrodes can be easily automated and the manufacturing cost can be reduced. Further, there is also an advantage such that the yield can be improved since the loss of material is little in the manufacturing steps.

On the other hand, with respect to the performance of the enzyme electrode, since the grinding and polishing steps of the electrode are not included in the manufacturing steps, cracks and gaps into which the liquid can enter are not formed in the peripheral portion of the electrode and the noise is reduced. In addition, since the area of each exposed portion is determined with the high accuracy of the photo mask and a number of enzyme electrodes can be together manufactured by the mass production, the areas of the electrode exposed portions are uniformed and a variation in output of the electrodes is reduced. Further, since the immobilized enzyme film is integratedly formed on the surface of the insulative base plate, a change in output due to the defective attachment of the immobilized enzyme film is small and the output is stabilized.

Although the working electrode and reference electrode have been made of the same material and the exposed portions of both electrodes have been covered by the immobilized enzyme film in the foregoing embodiments, it is sufficient to cover at least one of the exposed portions. The third embodiment in which at least one of the exposed portions is covered by the immobilized enzyme film and the working electrode and reference electrode can be made of different materials will now be described in detail hereinbelow with reference to FIGS. 11a to 11g and 12a to 12g.

Figure 11A:
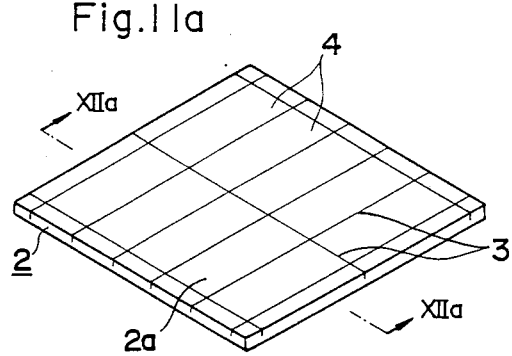
Figure 12A:
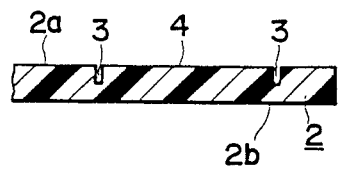

Referring to FIGS. 11a and 12a, the notches 3 are formed in the insulative flat plate 2 to form a plurality of segments 4 in a manner similar to the first and second embodiments. The alumina ceramic plate having a rough surface is used as the insulative flat plate 2 without finishing the surface like a mirror. The reasons why the insulative flat plate 2 having a rough surface is used are to increase the effective areas of the working electrode 5 and reference electrode 6 and to prevent that the acetyl cellulose film 13 is peeled off from the insulative base late 9.

Figure 11B:
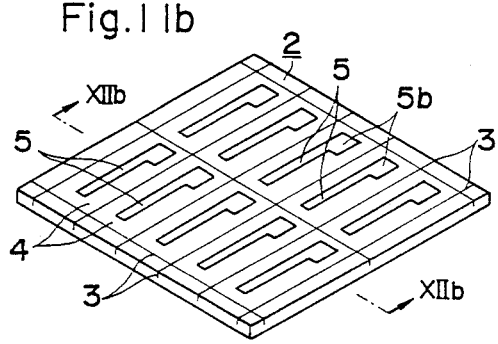
Figure 12B:
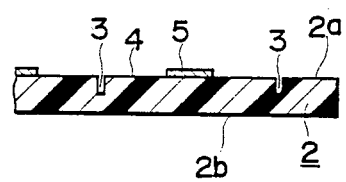

Referring now to FIGS. 11b and 12b, the working electrode 5 is formed on an upper surface 2a of the insulative flat plate 2 at each segment 4. The working electrode 5 is of the band-shaped platinum thin film (e.g., dimensions are 1×11mm and a thickness is 1500 Å) having a wide width portion serving as the connecting portion 5b and is formed by a sputtering. The working electrode 5 is formed by a photo resist method and the position and shape of the working electrode 5 are accurately determined by the photo mask.

Figure 11C:
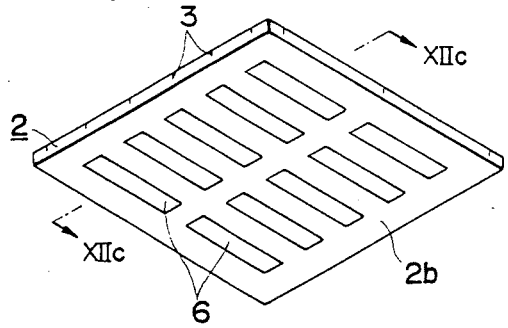
Figure 12C:
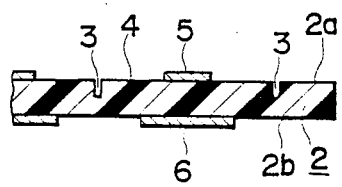
Figure 12D:
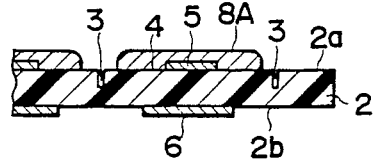
Figure 12E:
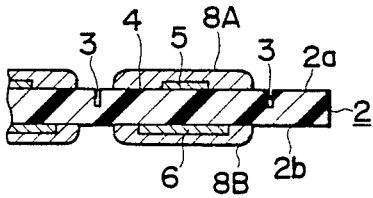

Referring to FIGS. 11c and 12c, the reference electrodes 6 are formed on a lower surface 2b of the insulative flat plate 2. The reference electrode 6 is the silver thin film (e.g., dimensions are 1.5×11mm) which is formed by the vacuum evaporation deposition. The reference electrode 6 is formed at the position corresponding to the working electrode 5 of the upper surface 2a of the insulative flat plate 2. The position and shape of the reference electrode 6 are accurately determined by the photo mask.

As mentioned above, the reason why the working electrode 5 and reference electrode 6 are separately formed on the upper surface 2a and lower surface 2b of the insulative flat plate 2 is to simplify the manufacturing steps. If a pair of working electrode and reference electrode made of different metal thin films are formed on one surface, the manufacturing steps are complicated. Although the steps are simplified by forming the working electrode and reference electrode by the same kind of metal thin film as in the first and second embodiments, the detecting performance of the enzyme electrode in the third embodiment in which different kinds of metals are used as the materials of the electrodes is further improved as compared with those in the first and second embodiments.

Referring to FIGS. 11d, 12d, 11e and 12e, insulative protection films 8A and 8B are formed on the upper and lower surfaces 2a and 2b of the flat plate 2 excluding the portions serving as the exposed portions 5a and 6a and the connecting portions 5b and 6b of the working electrode 5 and reference electrode 6, respectively. The ratio of areas of the exposed portions 5a and 6a is set to, e.g., 1:20.

Figure 11D:
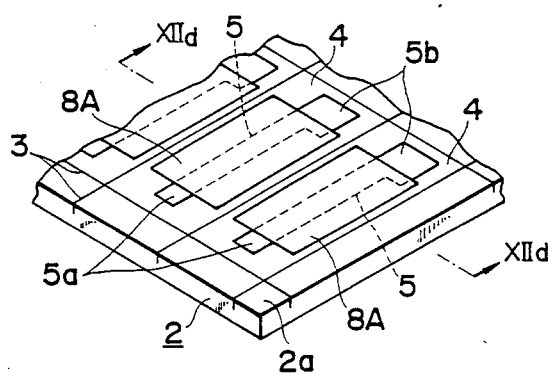
Figure 11E:
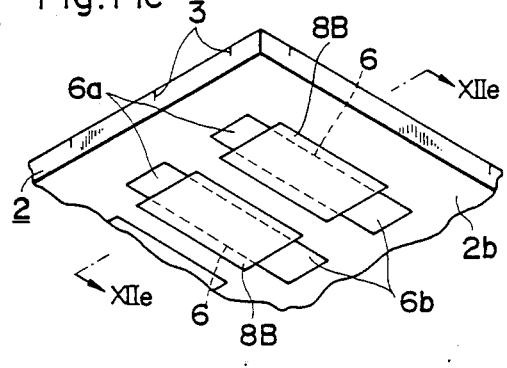
Figure 11F:
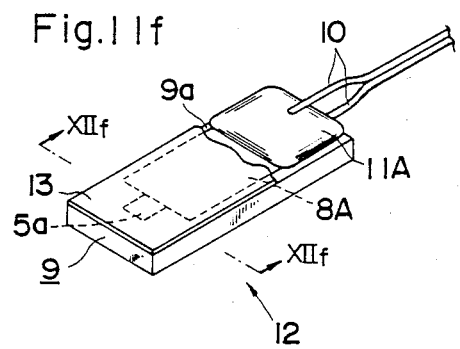
Figure 12F:
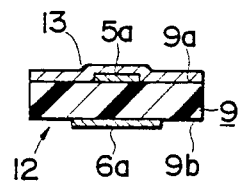

Referring to FIGS. 11f and 12f, the flat plate 2 is separated into a plurality of segments 4 along the notches 3 to form the insulative base plates 9. Lead wires 10 are soldered to the connecting portions 5b and 6b on upper and lower surfaces 9a and 9b of the base plate 9. The connecting portions 5b and 6b are covered by epoxy resins 11A and 11B, so that the unfinished electrode 12 is formed. The acetyl cellulose film 13 is formed on the upper surface 9a of the insulative base plate of the unfinished electrode 12 so as to completely cover the working electrode exposed portion 5a.

Referring to FIGS. 11g and 12g, the immobilized enzyme film 16 consisting of the acetyl cellulose film 13, enzyme layer 14, and acetyle cellulose film 15 is finally formed on only the upper surface 9a of the insulative base plate 9.

The characteristics of the unfinished electrode 12 and enzyme electrode 1 manufactured in this manner are shown in FIGS. 13 and 14. It will be understood from the characteristic of FIG. 13 that the proper value of the applied voltage falls within a range from 0.4 to 0.7 V. The electrode voltage was 0.6 V in the measurement of the characteristic of FIG. 14. The dimensions of the working electrode exposed portion 5a used were 1.0×0.5mm.

In the foregoing embodiments, only the working electrode exposed portion 5a has been covered by the immobilized enzyme film 16. However, the reference electrode exposed portion 6a may be also covered by the immobilized enzyme film.

Figure 15A:
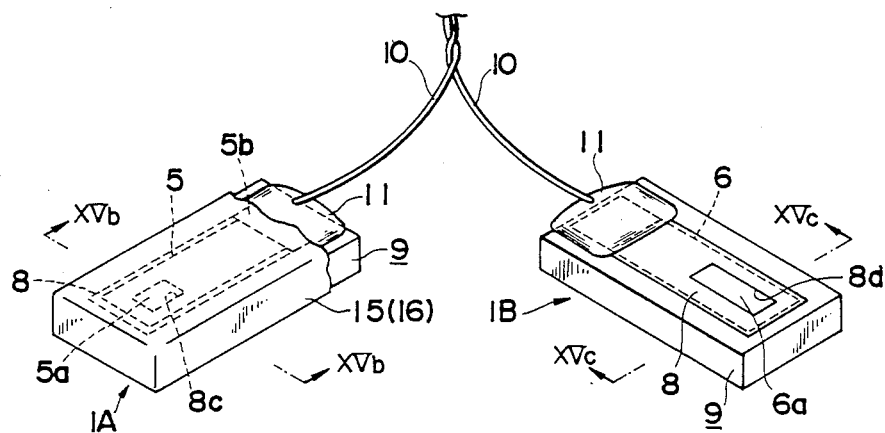
FIGS. 15a to 15c show an enzyme electrode of the fourth embodiment of the present invention.
Figure 15B:
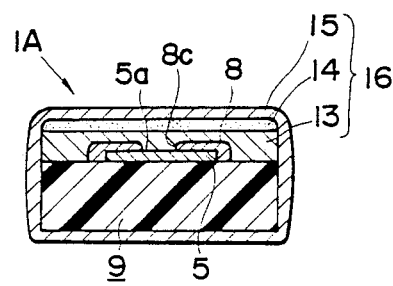
Figure 15C:
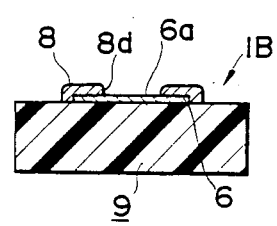
Figure 17A:
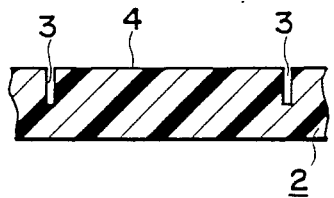
Figure 17B:
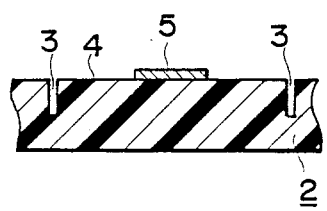

In the foregoing three embodiments, the working electrode and reference electrode are formed on one base plate irrespective of one surface or both surfaces of the base plate. FIGS. 15a to 15c show the fourth embodiment regarding an enzyme electrode in which the working electrode and reference electrode are formed on separate base plates, respectively. In these diagrams, the same parts and components as those shown in the first to third embodiments are designated by the same reference numerals. The enzyme electrode of the fourth embodiment comprises a working part 1A and a reference part 1B. A constitution of the working part 1A will now be described hereinbelow in accordance with the order of the manufacturing steps with reference to FIGS. 16a to 16e and 17a to 17e.

The working electrode 5 made of a platinum thin film having the portion serving as the connecting portion 5b at one end is formed by a sputtering onto each of the segments 4 divided by the notches 3 in the insulative flat plate 2. The electrode 5 is formed substantially like a rectangle of, e.g., 1×11mm (refer to FIGS. 16a, 17a, 16b and 17b).

Next, the insulative protection film 8 made of photosensitive polyimide is formed so as to cover the working electrode 5. The connecting portion 5b of the working electrode 5 is not covered by the protection film 8. A part of the working electrode 5 is exposed as the exposed portion 5a from the window 8c formed in the protection film 8. The window 8c is a square of, e.g., 0.2×0.2mm (FIGS. 16c and 17c).

Subsequently, the acetyl cellulose 13 and enzyme film 14 are laminated on the surface of insulative flat plate 2 (FIGS. 16d and 17d). First, the connecting portion 5b on the plate 2 is masked by a masking tape 18. The masked plate 2 is set to the spinner. The 3% acetyl cellulose solution is dropped onto the surface of the insulative flat plate. The plate 2 is rotated at 2,000 r.p.m. for five seconds. Thus, the acetyl cellulose solution uniformly spreads over the surface of the plate 2, so that the acetyl cellulose film 13 is formed.

Further, the same enzyme solution as that in the foregoing embodiments is dropped onto the acetyl cellulose film 13. The insulative flat plate 2 is similarly rotated. Thus, the enzyme film 14 is formed.

The plate 2 is detached from the spinner, and the masking tape 18 is peeled off. The working electrode connecting portion 5b is exposed. Thereafter, the plate 2 is separated into a plurality of individual insulative base plates 9 along the segment lines 3. The edge of the lead wire 10 is coupled with the connecting portion 5b by the ultrasonic bonding. The coupling portion is sealed and protected by the epoxy resin 11 (FIGS. 16e and 17e).

The insulative base plate 9 is dipped into the 2% acetyl cellulose solution (solvent composition acetone:ethanol=4:1), so that an acetyl cellulose film 15 is formed on the whole surface (refer to FIGS. 15a and 15b). The film 15 is provided to protect the enzyme film 14. The immobilized enzyme film 16 is constituted by the acetyl cellulose film 13, enzyme film 14 and acetyl cellulose film 15.

The reference part 1B is also manufactured by the similar steps. The window 8d of the insulative protection film 8 is formed like a rectangle of, e.g., 0.5×2.5mm. A part of the reference electrode 6 (having a rectangular shape of, e.g., 3×11mm) made of a silver thin film is exposed from the window 8d, thereby forming the exposed portion 6a. The insulative flat plate is separated into the insulative base plates 9. The lead wire 10 is connected to the reference electrode connecting portion 6b by the ultrasonic bonding and the coupling portion is sealed by the epoxy resin 11. In this manner, the reference part 1B is completed.

FIG. 18 shows the characteristic of the unfinished electrode which is constituted by the working part 1A from which the immobilized enzyme film 16 was eliminated and the reference part 1B. FIG. 19 shows the glucose detection characteristic of the enzyme electrode consisting of the working part 1A and reference part 1B. In FIG. 18, the parameters are the $H_2O_2$ concentrations (0, 1, 5, and 10 PPM) of the phosphoric acid buffer solution similarly to those in the foregoing embodiments. It will be understood from this graph that the proper value of the applied voltage falls within a range from 0.6 to 0.8 V. The electrode voltage applied in the measurement of the characteristic in FIG. 19 was 0.7 V.

In the enzyme electrode of the fourth embodiment, if the immobilized enzyme film deteriorated due to the use, it is sufficient to exchange only the insulative base plate (e.g., the working part) on which the deteriorated immobilized enzyme film is attached. The other insulative base plate (e.g., reference part) can be continuously used without exchanging. Therefore, there is an advantage such that this enzyme electrode is economical.

The enzyme electrode shown in each of the foregoing embodiments can measure only one kind of material. The fifth embodiment shown in FIG. 20 is suitable to measure two or more kinds of materials. In FIG. 20, the same parts and components as those shown in the foregoing embodiments are designated by the same reference numerals.

The enzyme electrode of the fifth embodiment is suitable to measure the concentrations of glucose and uric acid contained in the blood or the like. The enzyme electrode is constituted by attaching the working part 1A to detect glucose, a working part 1C to detect uric acid and the reference part 1B which is common to both of the working parts 1A and 1C onto a base plate 20.

The method of manufacturing the working part 1A to detect glucose is substantially the same as that shown in the fourth embodiment. However, in the fifth embodiment, the connecting portion 5b of the working electrode 5 is also exposed by forming a window into the insulative protection film 8. The working electrode 5 is made of a platinum thin film and its size is 1×11mm and a thickness is 1500 Å. The size of the exposed portion 5a is 0.15×2mm. The size of the connecting portion 5b is 1×2mm. Similarly to the foregoing embodiment, solution of the enzyme layer contained in the immobilized enzyme film 16 is formed by mixing the solution in which glucose oxidase (GOD) of 2 mg is dissolved into the 0.1 M phosphoric acid buffer solution (pH is 6.0) of 100 μl with the 0.5% glutaraldehyde solution of 100 μl adjusted by the same phosphoric acid buffer solution.

The working part 1C to detect uric acid has also the same constitution as that of the working part 1A excluding that the enzyme solutions differ. The enzyme solution which is used for the working part 1C is formed by mixing the solution in which uricase of 4 mg is dissolved in the 0.1 M phosphoric acid buffer solution (pH is 6.0) of 100 μl with the 0.5% glutaraldehyde solution of 100 μl.

The reference part 1B is the same as that in the fourth embodiment. A different point is that the connecting portion 6b of the reference electrode 6 is exposed by forming the window 8a in the insulative protection film 8. The reference electrode 6 is made of a silver thin film. For example, the size of the reference electrode 6 is 2×11mm. The size of the exposed portion 6a is 0.8×3mm. The size of the connecting portion 6b is 1×2mm.

The base plate 20 is merely a flat plate made of alumina ceramics or the like. The working part 1A, reference part 1B and working part 1C are adhered in parallel onto the base plate 20.

FIGS. 21 and 22 show the detection characteristics by the enzyme electrode mentioned above. The measuring system by which these characteristic data was obtained is the same as that shown in FIG. 5.

A predetermined amount of glucose solution or uric acid solution is dropped into the 0.1 M phosphoric acid buffer solution 50 in the constant temperature bath 49 by the micropipet.

$H_2O_2$ is produced by the foregoing reaction which occurs in the immobilized enzyme film 16 of the working part 1A. A current flows between the working electrode 5 of the working part 1A and the reference electrode 6 by $H_2O_2$. This current is measured for various kinds of glucose concentrations, so that a graph shown in FIG. 21 is obtained.

On the other hand, the following reaction is caused in the immobilized enzyme film 16 of the working part 1C by uric acid.

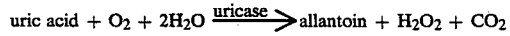

$$\text{uric acid} + O_2 + 2H_2O \xrightarrow{\text{uricase}} \text{allantoin} + H_2O_2 + CO_2$$

In response to $H_2O_2$ produced by this reaction, a current flows between the working electrode 5 of the working part 1C and the reference electrode 6. FIG. 22 is a graph in which the electrode outputs (nA) to the different uric acid concentrations (mg/dl) are plotted.

Even in the case where glucose and uric acid simultaneously exist in the liquid to be examined, a situation such that a measurement error occurs by the mutual interference of them is not caused.

In the fifth embodiment, there has been shown an enzyme electrode which has two working parts and one reference part and detects glucose and uric acid. However, the numbers of working parts and reference parts, combination thereof, kinds of enzyme used, etc. are not limited to those in this embodiment but can be properly changed. The enzyme electrode of the fifth embodiment has an advantage such that many items can be measured by the single enzyme electrode.

Since the insulative base plate of the enzyme electrode has been made of a hard material in each of the foregoing five embodiments, the insulative base plate cannot be changed into an arbitrary shape. An embodiment using a flexible base plate will now be described.

FIGS. 23a and 23b show the sixth embodiment. According to an enzyme electrode of this embodiment, a pair of conductor patterns 31 are formed on the surface of the flexible insulative base plate 19. One or two or more plating layers 32, 33 and 34 are laminated on the conductor patterns 31, thereby constituting the electrodes 5 and 6. The insulative protection film 8 to cover the portions other than the exposed portions 5a and 6a and connecting portions 5b and 6b of the electrodes 5 and 6 and the immobilized enzyme film 16 to cover at least one of the exposed portions 5a and 6a are formed on the base plate 19.

For example, a fluorine resin is used as the flexible base plate 19. The material of the flexible base plate 19 is not limited to this. For example, polycarbonate or acetyl cellulose can be also used and its size and shape are not limited to those shown in the diagrams.

The working electrode 5 and reference electrode 6 respectively comprise the exposed portions 5a and 6a, connecting portions 5b and 6b, and lead portions 5c and 6c. In order to form the electrodes 5 and 6, the conductor patterns (e.g., copper foils) 31 having the same shapes as those shapes are formed on the base plate 19. Three plating layers are overlapped and formed on the conductor patterns 31 by the electrolytic plating. First, the nickel plating layer 32 is formed on the conductor patterns 31. The thickness of the nickel plating layer 32 is about 1 μm. A gold plating layer 33 is formed on the nickel plating layer 32. The thickness of the gold plating layer 33 is also about 1 μm. The platinum plating layer 34 is further formed on the gold plating layer 33. The reason why three plating layers 32, 33 and 34 are laminated in this manner is because platinum cannot be directly plated on the conductor patterns 31 made of copper.

In this embodiment, in the working electrode 5, the size of the exposed portion 5a is 1×1mm, a width of the lead portion 5c is 0.5 mm, and the size of the connecting portion 5b is 2×7mm. However, these dimensions are not limited to these values. In the reference electrode 6, the exposed portion 6a has substantially an L-shape and its length is 6 mm and its width is 3 mm. The sizes of the lead portion 6c and connecting portion 6b are the same as those of the lead portion 5c and connecting portion 5b of the working electrode 5.

The insulative film (insulative protection film) 8 is adhered onto the insulative base plate 19, so that the working electrode lead portion 5c and reference electrode lead portion 6c are insulated and protected. On the other hand, the edges of the lead wires 10 are respectively soldered to the working electrode connecting portion 5b and reference electrode connecting portion 6b and the connecting portions are covered by an epoxy resin (not shown). The immobilized enzyme film 16 consisting of the acetyl cellulose film 13, enzyme layer or film 14 and acetyl cellulose film 15 is formed on the exposed portions 5a and 6a of the working electrode 5 and reference electrode 6.

According to the enzyme electrode of this embodiment, since the insulative base plate is flexible, the shape of the enzyme electrode can be changed and attached in accordance with the shape of the base which is used; therefore, this enzyme electrode is excellent in easiness of use.

FIGS. 24a and 24b show the seventh embodiment. In these diagrams, the same parts and components as those shown in FIGS. 23a and 23b are designated by the same reference numerals. According to an enzyme electrode of this embodiment, two or more electrodes 5 and 6 made of a conductive paste 41 having respectively the exposed portions 5a and 6a and connecting portions 5b and 6b are provided on the surface of the flexible insulative base plate 19. Another conductor film 42 is laminated on the exposed portion 5a of at least one electrode 5 of the electrodes 5 and 6. The portions other than the exposed portions 5a and 6a and connecting portions 5b and 6b of the electrodes 5 and 6 are covered by the insulative protection film 8. The exposed portion 5a on which at least the conductor film 42 is laminated is covered by the immobilized enzyme film 16.

Explaining in further detail, the silver paste (conductive paste) 41 is directly printed onto the surface of the flexible base plate 19 and the working electrode 5 and reference electrode 6 are formed. The thickness of the silver paste 41 is, e.g., about 10 μm.

The platinum foil (conductor film) 42 is thermally pressure bonded (hot stamped) onto the exposed portion 5a of the working electrode 5 by a hot plate, or the platinum foil (metal foil) is adhered by use of a conductive adhesive agent. The thickness of the platinum foil 42 is, e.g., 5 μm.

The insulative protection film 8 is formed so as to cover the exposed portion 5a and lead portion 5c of the working electrode 5 and the lead portion 6c of the reference electrode 6. The window 8c is formed in the protection film 8 over the exposed portion 5a, thereby exposing the exposed portion 5a.

The connecting portions 5b and 6b to which the lead wires 10 are connected are covered by the epoxy resin 11 and the exposed portions 5a and 6b are covered by the immobilized enzyme film 16 in a manner similar to the foregoing embodiments.

Although two electrodes (working electrode 5 and reference electrode 6) have been formed on the base plate in this embodiment, the number of electrodes is not limited to two. In addition, the shapes of the electrodes and the number of exposed portions provided for one electrode and the like can be also arbitrarily changed.

What is claimed is:

1. An enzyme electrode comprising:
   an insulative base;
   at least two electrodes including a working electrode and a reference electrode provided on the surface of said insulative base and each having an exposed portion and a connecting portion, the area of the exposed portion of the reference electrode being larger than that of the exposed portion of the working electrode;
   an insulative protection film covering the portions excluding said exposed portions and connecting portions of said electrodes; and
   an immobilized enzyme film which covers integrally at least the exposed portions of said working electrode.

2. An enzyme electrode according to claim 1, wherein windows are formed in said insulative protection film and parts of said electrodes are exposed from said windows, thereby forming said exposed portions and connecting portions.

3. An enzyme electrode according to claim 1, wherein said insulative protection film is made of a photosensitive resin.

4. An enzyme electrode according to claim 4, wherein the electrodes are respectively formed on at least two surfaces of said insulative base.

5. An enzyme electrode according to claim 1, wherein said insulative base consists of a flexible insulative base plate, and said electrode comprises conductor patterns formed on the surface of said base plate and one or two or more plating layers laminated on said conductor patterns.

6. An enzyme electrode according to claim 1, wherein said insulative base consists of a flexible insulative base plate, said electrodes are made of conductive pastes formed on said base plate, another conductor film is laminated on the exposed portion of at least one of said electrodes, and the exposed portion onto which at least said conductor film is laminated is covered by the immobilized enzyme film.

7. An enzyme electrode according to claim 1, wherein said insulative base consists of a flexible insulative base plate, said electrodes are made of conductive pastes formed on said insulative base plate, a metal foil is adhered onto the exposed portion of at least one of the electrodes by a conductive adhesive agent, and the exposed portion on which at least said metal foil is adhered is covered by the immobilized enzyme film.

8. An enzyme electrode according to claim 1, wherein said insulative base is a flexible insulative base.

9. An enzyme electrode according to claim 1, wherein the area of the exposed portion of the reference electrode is at least 20 times as large as that of the exposed portion of the working electrode.

10. An enzyme electrode according to claim 1, wherein the working electrode, the reference electrode, the insulative protection film and the immobilized enzyme film are integrally fabricated on the insulative base.

11. A combination enzyme electrode, comprising:
    a pair of insulative bases;
    a working electrode provided on the surface of one of said insulative bases and a reference electrode provided on the surface of the other of said insulative bases, each of said working electrode and said reference electrode having an exposed portion and a connecting portion, the area of the exposed portion of said reference electrode being larger than that of the exposed portion of said working electrode;
    insulative protection films covering the portions of said insulative bases excluding said exposed portions and connecting portions of said electrodes; and
    an immobilized enzyme film which integrally covers the exposed portion of said working electrode.

12. An enzyme electrode according to claim 11, wherein the area of the exposed portion of the reference electrode is at least 20 times as large as that of the exposed portion of the working electrode.

13. An enzyme electrode according to claim 11, wherein the working electrode, the reference electrode, the insulative protection films and the immobilized enzyme film are integrally fabricated on the respective insulative bases.

14. An enzyme electrode comprising:
    an insulative base plate;
    two or more electrodes provided on the surface of said insulative base plate and each having an exposed portion;
    an insulative protection film insulating and protecting said electrodes except for said exposed portions; and
    an immobilized enzyme film which integrally covers said exposed portion of at least one of said electrodes, said immobilized enzyme film comprising a first protective film formed on the portion including said exposed portion for preventing said electrode from sensing interfering materials, an enzyme film, and a second protective film for covering said enzyme film, said enzyme film being sandwiched between said first and second protective films.

15. An enzyme electrode according to claim 14, wherein said first and second protective films are acetyl cellulose films.

16. An enzyme electrode according to claim 14, wherein the area of the exposed portion of the reference electrode is at least 20 times as large as that of the exposed portion of the working electrode.

17. An enzyme electrode according to claim 14, wherein the working electrode, the reference electrode, the insulative protection film and the immobilized enzyme film are integrally fabricated on the insulative base.

18. An enzyme electrode comprising:
an insulative base plate;
an electrode provided on the surface of said insulative base plate and having an exposed portion;
an insulative protection film which insulates and protects said electrodes except for said exposed portion; and
an immobilized enzyme film which integrally covers said exposed portion of at least one of said electrodes, said immobilized enzyme film comprising a first protective film formed on the portion including said exposed portion for preventing said electrode from sensing interfering materials, an enzyme film, and a second protective film for covering said enzyme film, said enzyme film being sandwiched between said first and second protective films.

19. An enzyme electrode according to claim 18, wherein the area of the exposed portion of the reference electrode is at least 20 times as large as that of the exposed portion of the working electrode.

20. An enzyme electrode according to claim 18, wherein the working electrode, the reference electrode, the insulative protection film and the immobilized enzyme film are integrally fabricated on the insulative base.

* * * * *